United States Patent
Iwanaga

(10) Patent No.: US 9,022,567 B2
(45) Date of Patent: May 5, 2015

(54) OPHTHALMIC IMAGING APPARATUS AND CONTROL METHOD THEREOF

(71) Applicant: Canon Kabushiki Kaisha, Tokyo (JP)

(72) Inventor: Tomoyuki Iwanaga, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/108,484

(22) Filed: Dec. 17, 2013

(65) Prior Publication Data

US 2014/0104573 A1     Apr. 17, 2014

Related U.S. Application Data

(63) Continuation of application No. 13/927,254, filed on Jun. 26, 2013, now Pat. No. 8,636,362, which is a continuation of application No. 13/103,473, filed on May 9, 2011, now Pat. No. 8,567,947.

(30) Foreign Application Priority Data

Jun. 1, 2010 (JP) ................. 2010-126293

(51) Int. Cl.
- *A61B 3/14* (2006.01)
- *A61B 3/12* (2006.01)
- *A61B 3/00* (2006.01)

(52) U.S. Cl.
CPC . *A61B 3/145* (2013.01); *A61B 3/14* (2013.01); *A61B 3/12* (2013.01); *A61B 3/0025* (2013.01)

(58) Field of Classification Search
USPC .................. 351/206, 246, 209, 205, 210
See application file for complete search history.

(56) References Cited

U.S. PATENT DOCUMENTS

| | | | |
|---|---|---|---|
| 5,894,337 A | 4/1999 | Okinishi et al. | |
| 6,192,269 B1 | 2/2001 | Okumura et al. | |
| 6,324,420 B1 | 11/2001 | Kishida et al. | |
| 6,494,577 B2 | 12/2002 | Iwanaga | |
| 7,235,051 B2 | 6/2007 | Iwanaga | |
| 2009/0244483 A1 | 10/2009 | Yoshino et al. | |
| 2011/0007272 A1* | 1/2011 | Sekiguchi et al. | 351/206 |
| 2011/0292337 A1 | 12/2011 | Iwanaga | |
| 2013/0027664 A1 | 1/2013 | Kishida | |

FOREIGN PATENT DOCUMENTS

| | | |
|---|---|---|
| JP | 60-057853 B2 | 12/1985 |
| JP | 05-095905 A | 4/1993 |
| JP | 06-013022 B2 | 2/1994 |
| JP | 2009-066109 A | 4/2009 |
| JP | 2009-131591 A | 6/2009 |

\* cited by examiner

*Primary Examiner* — Hung Dang
(74) *Attorney, Agent, or Firm* — Fitzpatrick, Cella, Harper & Scinto

(57) ABSTRACT

An ophthalmic imaging apparatus divides a frame image obtained by capturing a moving image into a plurality of regions grouping pixels, and acquires photometric values corresponding the plurality of the regions. Further, the ophthalmic imaging apparatus determines acknowledgement or dis-acknowledgement of capturing a still image based on temporal variation of the acquired photometric values or distribution of the acquired photometric values on a fundus image. The ophthalmic imaging apparatus inhibits to execute a still image capturing of the fundus if the dis-acknowledgement of capturing is determined.

21 Claims, 7 Drawing Sheets

OPHTHALMIC IMAGING APPARATUS AND CONTROL METHOD THEREOF

This application is a continuation of application Ser. No. 13/927,254 filed Jun. 26, 2013, now U.S. Pat. No. 8,636,362, which is a continuation of application Ser. No. 13/103,473 filed May 9, 2011, U.S. Pat. No. 8,567,947 B2

BACKGROUND OF THE INVENTION

1. Field of the Invention

The present invention relates to an ophthalmic imaging apparatus having blink detection function and control method thereof.

2. Description of the Related Art

Regarding a fundus camera as an ophthalmic imaging apparatus, the fundus camera having a blink function is proposed. The fundus camera detecting the blink is described in Japanese Patent No. 60-057853 (hereafter, document 1) by disposing a special photo-detection means at the position, receiving reflected light from an anterior segment of the eye to be examined in the fundus camera optic system, and detecting change in the quantity of reflected light. Moreover, the ophthalmic imaging apparatus proposed in Japanese Patent No. 06-013022 (hereafter, document 2) obtains a fundus image illuminated by near-infrared light emitted from an observation light source, by using a two-dimensional image sensing device and a blink is detected by an outgoing signal of the fundus image. According to the detection result, the ophthalmic imaging apparatus permits or prohibits obtaining the fundus image by a separated imaging means.

In addition, a fundus camera, which obtains an image of an object by an image sensing device and controls an aperture of the optical system by using the signal of the image, is proposed. A fundus camera proposed in Japanese Patent Laid-Open No. 08-001022 (hereafter, document 3) changes the size of the shading part installed in the state of optical conjugate with the anterior segment of the eye to be examined in illumination optics according to the result of the means for inputting or detecting a pupil diameter of the eye to be examined, and can illuminate even the small pupil system.

However, there has been a problem in that the device configuration becomes complicated to provide the blink detection function in the fundus cameras described in document 1 and document 2 mentioned above. For instance, a special blink detection sensor is necessary in the fundus camera that has the blink detection function described in document 1. Moreover, in the fundus camera described in document 2, even though the observation image sensing device that outputs the moving image and the means for blink detection are shared, a capturing means for still image is separately needed.

In addition, the detection accuracy decreases if the imaging means and detection sensors are separately arranged and there is a relative position misalignment between imaging means and detection sensors, as mentioned above. Therefore, it is necessary to apply severe accuracy to each component or to perform adjustment work by using the adjustment mechanism to eliminate relative position misalignment. As a result, the cost of the device rises.

In addition, a means for detecting a pupil diameter is also necessary for the fundus camera, which changes a light blocking part that is arranged in an illumination optical system according to the pupil diameter of the eye to be examined described in document 3. Therefore, when combining with blink detection function mentioned above, the structure of the fundus camera may be complicated. Moreover, when the means for inputting the pupil diameter is used, instead of means for detecting the pupil diameter, a problem rises where inappropriate image capturing may be performed because of an increase of user's operations and user's input error.

SUMMARY OF THE INVENTION

In order to solve the above problems, one of the embodiments of the present invention provides an ophthalmic imaging apparatus, with a simple structure that enables blink detection.

According to one aspect of the present invention, there is provided an ophthalmic imaging apparatus comprising: an imaging unit configured to execute moving image capturing and still image capturing to obtain a moving image and a still image of a fundus image; an acquisition unit configured to divide a frame image of the moving image obtained by the moving image capturing, into a plurality of regions grouping pixels and acquire photometric values corresponding a plurality of the regions; a determination unit configured to determine acknowledgement or dis-acknowledgement of the still image capturing based on temporal variation of the photometric values or distribution of the photometric values on the fundus image; and a control unit configured to inhibit the imaging unit from executing the still image capturing if the dis-acknowledgement is determined by the determining unit.

According to another aspect of the present invention, there is provided method of controlling an ophthalmic imaging apparatus comprising an imaging unit configured to execute moving image capturing and still image capturing to obtain a moving image and a still image of a fundus image, the method comprising the steps of: dividing a frame image of the moving image obtained by the moving image capturing into a plurality of regions grouping pixels; acquiring photometric values corresponding a plurality of the regions; determining acknowledgement or dis-acknowledgement of the still image capturing based on temporal variation of the photometric values or distribution of the photometric values on the fundus image; and inhibiting the imaging unit from executing the still image capturing if the dis-acknowledgement is determined in the determining step.

Further features of the present invention will become apparent from the following description of exemplary embodiments with reference to the attached drawings.

DESCRIPTION OF THE EMBODIMENTS

Further features of the present invention will become apparent from the following description of exemplary embodiments with reference to the attached drawings.

First Embodiment

Figure 1:
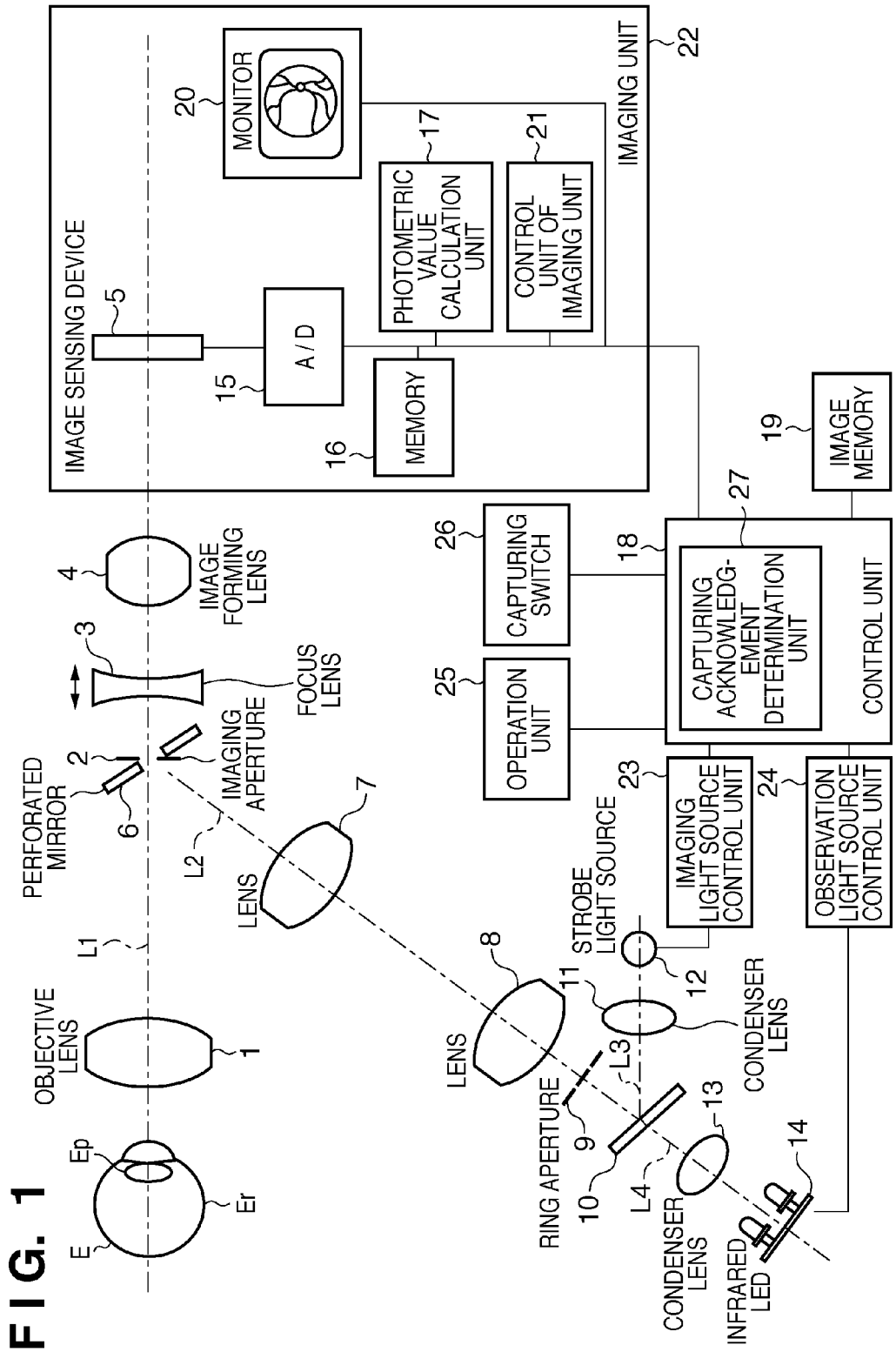
FIG. 1 shows an exemplary configuration for ophthalmic imaging apparatus in first embodiment.

FIG. 1 shows an exemplary configuration for ophthalmic imaging apparatus (hereafter, a fundus camera) in first embodiment. As shown in FIG. 1, an objective lens 1 is placed corresponding to an eye E to be examined, and an imaging aperture 2, a focus lens 3, an image forming lens 4 and an image sensing device 5 having sensitivity of visible light and infrared light are disposed on an optical axis L1. An observation/imaging optical system is configured by a set of lenses from the objective lens 1 to an image forming lens 4, and an observation/imaging unit of fundus image is configured by combining the image sensing device 5 with the set of lenses.

Further, a perforated mirror 6 is placed at a tilt near the imaging aperture 2. A set of lenses 7, 8, a ring aperture 9 having a ring-shaped aperture and a dichroic mirror 10 are disposed on an optical axis L2 in the direction reflected from the perforated mirror 6, wherein the dichroic mirror 10 has characteristic of passing infrared light and reflecting visible light. Here, the ring aperture 9 is allocated at an optically conjugated position for the pupil Ep of the eye E with respect to the objective lens 1, the lens 7 and the lens 8, and has a light blocking part at the center of the optical axis. Further, a condenser lens 11 and a strobe light source 12 emitting pulsed visible light are allocated on the optical axis L3 in the reflected direction from a dichroic mirror 10. A condenser lens 13 and an infrared LED 14 including a plurality of LEDs emitting continuous infrared light are arranged on an optical axis L4 toward the passing direction of the dichroic mirror 10. A fundus illumination optical system comprises the set of lenses, from the objective lens 1 to the dichroic mirror 10, a condenser lens 11 and a condenser lens 13. A fundus illumination unit comprises the fundus illumination optical system, a strobe light source 12 and the infrared LED 14.

As described above, an optical unit of the fundus camera is configured by an observation/imaging optical system and the fundus illumination unit for a fundus image, and for example, they are accommodated in one body. Further, the optical unit of the fundus camera is mounted on a sliding platform, not shown in the figure and it can be aligned with the eye E.

Further, the output of the image sensing device 5 is digitalized using an A/D converter 15 and stored in a memory 16. The digital signal converted by the A/D converter 15 is provided to a photometric value calculation unit 17 and the photometric value calculation unit 17 calculates and outputs a photometric value by a process described later. A monitor 20 displays an infrared image, a visible image and others, acquired by the image sensing device 5. A control unit 21 of imaging unit 22 integrates and controls each unit as described above. The imaging unit 22 comprises the image sensing device 5, the A/D converter 15, the memory 16, the photometric value calculation unit 17, the monitor 20 and the control unit 21. This imaging unit 22 is detachably fixed in the body of the optical unit of the fundus camera with a mount unit, not shown in the figure. In addition, each portion of the imaging unit 22 is connected with the control unit 18 that has a CPU and others that control the entire apparatus. An image memory 19 is connected with control unit 18, and a still image obtained by image sensing device 5 is saved as a digital image in the image memory 19.

On the other hand, the strobe light source 12 is connected to an imaging light source control unit 23, and the infrared LED 14 is connected to an observation light source control unit 24. Further, the imaging light source control unit 23, and the observation light source control unit 24 are connected to the control unit 18. In addition, the control unit 18 is connected to an operation unit 25, which sets an imaging condition such as observation light amount, a capturing light amount and others, and a capturing switch 26. Moreover, the control unit 18 comprises a capturing acknowledgement determination unit 27, which determines whether capturing should be permitted based on the output of the photometric value calculation unit 17.

Next, the operations of the fundus camera having the above structure in this embodiment are described. Light emitted from the infrared LED 14 is collected by the condenser lens 13 and after passing through the dichroic mirror 10, the light is constrained in ring-shape by the ring aperture 9. The light constrained by the ring aperture 9 forms an image of the ring aperture 9 on the perforated mirror 6 through the lens 8 and lens 7. The image formed on the perforated mirror 6 is reflected toward the optical axis L1, and again forms the image of ring aperture 9 near the pupil Ep of the eye E, by which the fundus Er of the eye E is illuminated.

A light beam exits the eye E from the pupil Ep, wherein the light beam is reflected and scattered from the fundus Er, which is illuminated by the infrared LED 14 emitting continuous light. Further, it reaches the image sensing device 5 through the objective lens 1, the imaging aperture 2, the focus lens 3 and the image forming lens 4, and it is captured by the image sensing device 5. In capturing an observation image, a moving image is captured by using the image sensing device 5. After the image signal output from the image sensing device 5 is digitalized by the A/D converter 15, the image signal is displayed on the monitor 20 as a fundus observation image (moving image) by the control unit 21 of imaging unit 22.

An examiner adjusts the light amount of the infrared LED 14 so that the fundus image displayed on the monitor 20 has proper brightness by operation unit 25, and aligns the eye E with the optical unit of the fundus camera by operating the joystick not shown in the figure. Further, the examiner adjusts the position of the focus lens 3 toward the optical axis by operating a focus knob, not shown in figure, in order to focus the fundus image. In addition, after operating the capturing switch 26, the strobe light source 12 emits light and the image sensing device 5 captures a still image, and a fundus image for medical examination is obtained.

Figure 2:
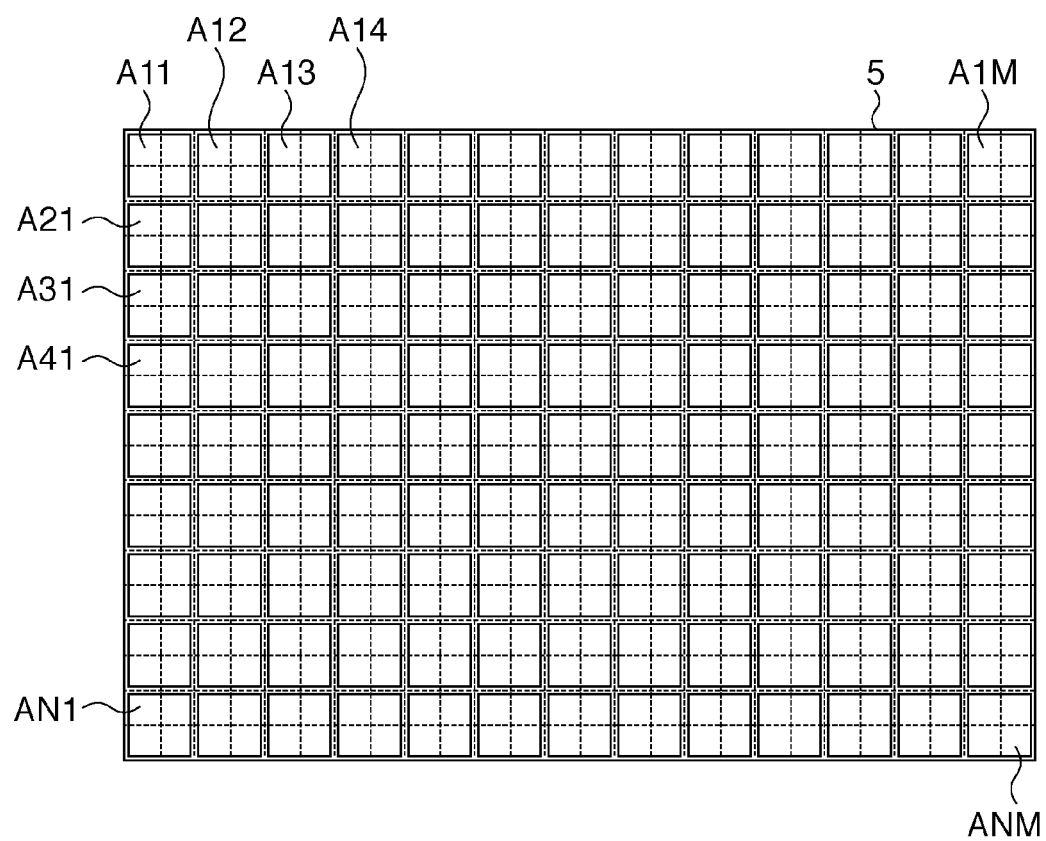
FIG. 2 shows a photometry region on an image sensing device.
Figure 3:
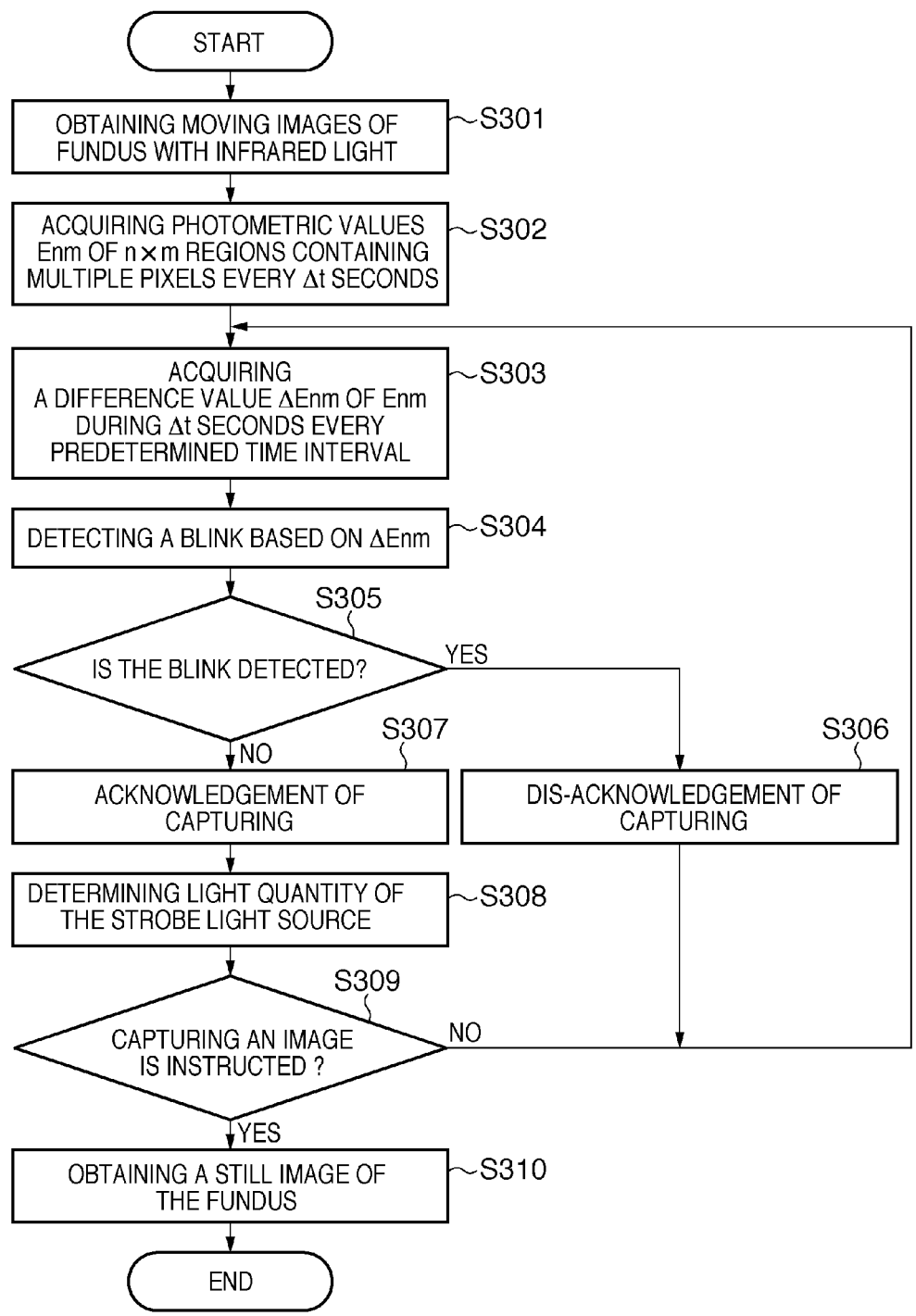
FIG. 3 shows a flow chart indicating fundus image processing in the first embodiment.

Next, referring to FIG. 2 and FIG. 3, the operation of the fundus camera in this embodiment is described including the detailed control of the photometric value calculation unit 17 and the capturing acknowledgement determination unit 27. At S301, the control unit 18 controls the observation light source control unit 24 and the control unit 21 to make the infrared LED 14 to generate infrared light as an observation light, and captures a moving image under the infrared light by the image sensing device 5. The photometric value calculation unit 17 divides a frame image obtained by the moving image into a plurality of photometric regions grouped with multiple pixels to provide a photometric value corresponding to the plurality of photometric regions every Δt seconds. Thus, the photometric value calculation unit 17 in this embodiment obtains the photometric value corresponding to the plurality of photometric regions from one frame of the image every Δt seconds. Accordingly, at S302, the control unit 18 obtains the photometric value output from the photometric value calculation unit 17 every Δt seconds.

FIG. 2 shows a pattern diagram indicating pixels of the image sensing device 5. The output from the image sensing device 5 is converted to a digital signal by the A/D converter 15 and is temporarily stored in the memory 16. The photometric value calculation unit 17 divides pixels in the image stored in the memory 16 into groups so that each group has a plurality of pixels; for example, as shown in FIG. 2, the pixels in the image are divided into N×M regions composed of A11, A12, A13 ..., A21 ..., A31 ..., A41 .... Meanwhile, although each group has 2×2 pixels (4 pixels) in FIG. 2, the way of dividing is not limited to the 2×2 pixels. Further, the photometric value calculation unit 17 outputs a mean pixel value within each region as the photometric value Enm to the control unit 18. The photometric value calculation unit 17 outputs each photometric value Enm every Δt seconds.

The control unit 18 transfers the photometric value Enm to the capturing acknowledgement determination unit 27. The capturing acknowledgement determination unit 27 calculates the amount of temporal variation in each photometric value Enm for Δt seconds (for example, every ⅕ seconds), ΔEnm=Enm (t=T+Δt)−Enm (t=T) (S303). Further, the capturing acknowledgement determination unit 27 detects a blink based on the calculated ΔEnm (S304). For instance, if there is at least one of the calculated temporal variation (ΔEnm) that is larger than the predetermined value, the capturing acknowledgement determination unit 27 determines that the temporal variation is caused by a blink and returns a capturing dis-acknowledgement to the control unit 18 (S305 (YES), S306). If all the calculated temporal variation (ΔEnm) is smaller than the predetermined value, that is, if there is no calculated amount that is equal to or more than the predetermined value, the capturing acknowledgement determination unit 27 determines that a blink did not happen and returns to a capturing acknowledgement to the control unit 18 (S305 (NO), S307).

In addition, in the determining of the capturing acknowledgement or dis-acknowledgement of (the determination for existence or nonexistence of a blink) as mentioned above, the capturing acknowledgement determination unit 27 may not determine a capturing dis-acknowledgement when the number of temporal variation ΔEnm that are more than the predetermined value within an N×M number of temporal variation ΔEnm, is less than the predetermined number, for example, the number of temporal variation ΔEnm that are more than the predetermined value is equal to or smaller than 10% of the N×M. In this way, the possibility of false detection of a blink can be reduced if the ΔEnm becomes more than the predetermined value due to the effect of electrical noise and others.

Moreover, control unit 18 determines the light amount in the strobe light source 12 based on each photometric value Enm and the control state of the observation light source control unit 24, and controls the imaging light source control unit 23 (S308). Further, for example, the control state of observation light source control unit 24 is a state of the light amount control of the infrared LED 14, and more specifically, it is a current value or a voltage and others applied to infrared LED 14. Moreover, the photometric value Enm during detection of the blink is not used for determining the light amount. In this embodiment, the light amount is determined only when the output from the capturing acknowledgement determination unit 27 indicates capturing acknowledgement (S308). Then the light amount of the strobe light source 12 is not determined based on the photometric value at the time when the output from the capturing acknowledgement determination unit 27 indicates capturing dis-acknowledgement.

Further, in this embodiment, the capturing acknowledgement determination unit 27 calculates the time variance of the photometric value Enm during the Δt second as temporal variation, and determines the capturing acknowledgement comparing the calculated photometric value with the predetermined value. However, the way of determination is limited to the above structure. For instance, the temporal moving average value of Enm output from the photometric value calculation unit 17 every Δt seconds is obtained, and it may be compared, as the temporal variation ΔEnm of the photometric value of each region Anm, with the predetermined value.

Moreover, it is normal that the top eyelid falls downward when the eye E blinks. At this time, the optical system of the fundus camera has the characteristic in which the observation/imaging light beam is interrupted from the bottom side of the fundus by the top eyelid. Further, the illumination light beam reflected and scattered by the top eyelid reaches the spot of the lower part of the fundus image within the image sensing device 5, and it is imaged considerably brighter than the fundus images. Therefore, in accordance with the blink of eye E, the photometric value Enm becomes sequentially larger from the region (the side of the top eyelid) where the lower part of the fundus image is located. In this way, the capturing acknowledgement determination unit 27 may determine that there exists a blink and may return the output of capturing dis-acknowledgement to the control unit 18 if the photometric value Enm becomes sequentially larger from the region where the lower part of the fundus image is located, even if the ΔEnm of the temporal variation of the photometric value is not larger than the predetermined value.

Next, when the alignment and the focus adjustment are completed, the operator pushes the capturing switch 26. The control unit 18 obtains a still image of the fundus if the capturing acknowledgement determination unit 27 already determines the capturing acknowledgement when the capturing switch 26 is pushed (S309, S310). That is, the control unit 18 controls the imaging light source control unit 23 to make the strobe light source 12 emit pulsed light with the light quantity determined at S308, and controls the control unit 21 of imaging unit 22 to capture using the image sensing device 5.

The operation when capturing a still image will be described. After the light beam (pulsed light) emitted from the strobe light source 12 is collected by the condenser lens 11 and reflected by the dichroic mirror 10, the light beam is constrained in a ring shape by the ring aperture 9. The light constrained by the ring aperture 9 forms an image of the ring aperture 9 on the perforated mirror 6 through the lens 8 and lens 7. This image is reflected toward the optical axis L1 by the perforated mirror 6, and again forms the image of the ring aperture 9 near the pupil Ep of the eye E, by which the fundus Er of the eye E is illuminated.

The light beam reflected and scattered from the fundus Er illuminated by the strobe light source 12 exits the eye E from the pupil Ep, and reaches the image sensing device 5 through the objective lens 1, imaging aperture 2, focus lens 3 and image forming lens 4. The image signal obtained by the image sensing device 5 is digitalized by the A/D converter 15, and the digitalized signal is stored as a still image in the memory 19.

On the other hand, the control unit 18 stops the imaging light source control unit 23 and inhibits the emission of the strobe light source 12 if the output of the capturing acknowledgement determination unit 27 indicates the capturing dis-acknowledgement. The output (capturing acknowledgement or dis-acknowledgement) of the capturing acknowledgement determination unit 27 is returned to the control unit 18 every ⅕ seconds as mentioned above. Therefore, the control unit 18 can obtain a still image at S310 after verifying that the blinking of the eye E is complete and the output of the capturing acknowledgement determination unit 27 indicates the capturing acknowledgement when the capturing order by a user has been received in the state of the capturing dis-acknowledgement (when the capturing switch 26 is pushed in the state of the capturing dis-acknowledgement). That is, even if the capturing dis-acknowledgement is determined when the capturing switch 26 is pushed, the operation of capturing automatically starts again when blinking is not detected. Therefore, it is possible to efficiently obtain excellent images of the fundus. In this way, the control unit 18 determines the light quantity of the observation light source unit 12 based on each photometric value Enm and the control state of the observation light source control unit 24, controls an imaging light source control unit 23 to allow the strobe light source 12 to emit pulsed light. Then the control unit 18 obtains the fundus image by using the image sensing device 5 and stores it as a still image in the image memory 19.

As mentioned above, in the first embodiment, the photometric value calculation unit 17 divides a frame image obtained by the image sensing device 5 into a plurality of regions grouped with multiple pixels and generates a photometric value corresponding to the plurality of regions based on the reflected light from the fundus illuminated by the observation light source. The control unit 18 determines the light quantity of the imaging light source based on the photometric value obtained by the photometric value calculation unit 17, and determines the capturing acknowledgement/dis-acknowledgement based on the temporal variation of the photometric value or the distribution of the photometric values in the plurality of the regions. Thus, the apparatus can be prevented from being complicated and can eliminate the relative misalignment of each image sensing device and the sensor by sharing an image sensing device for observation with an image sensing device for photometry. Therefore, the apparatus can provide an accurate automatic capturing light amount control and blink detection without increasing the cost, and can provide a fundus image having excellent brightness without capturing failure. Moreover, the apparatus can avoid myosis and useless energy consumption because it can prevent useless light irradiation to the eye to be examined.

In addition, although the observation light source emitting continuous light and the imaging light source emitting pulsed light are configured separately, an LED or the like, which can emit both continuous light and pulsed light, may be used as a light source. In this way, the configuration of the apparatus can be simplified.

Second Embodiment

There may be a negative effect where the central area of the fundus image is obtained in the dark if there is a reflection of illuminating light around the fundus image from the eye to be examined and this affects the light amount setting of the imaging light source. To solve this problem, in the second embodiment, a structure of the fundus camera, which can obtain a central area of the fundus image having excellent brightness even if there is reflection of illumination light around the fundus image from the examined eye, is described. The apparatus configuration of the fundus camera of the second embodiment is similar to that of the first embodiment (FIG. 1).

Figure 4:
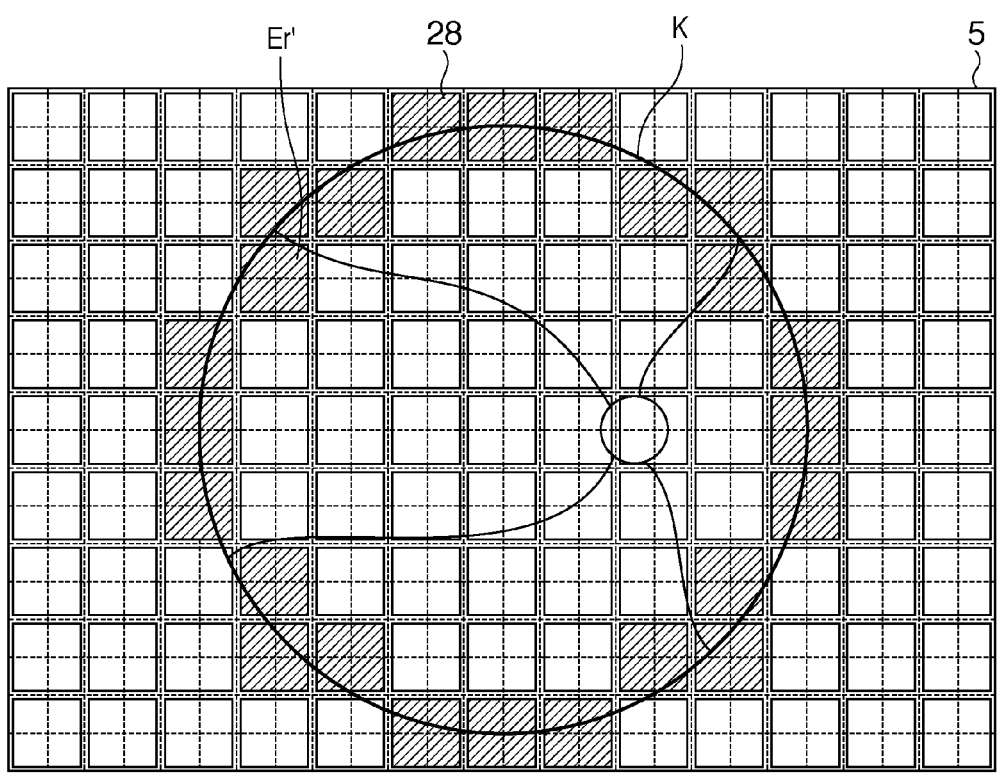
FIG. 4 shows a photometry region and fundus image Er' on the image sensing device.
Figure 5:
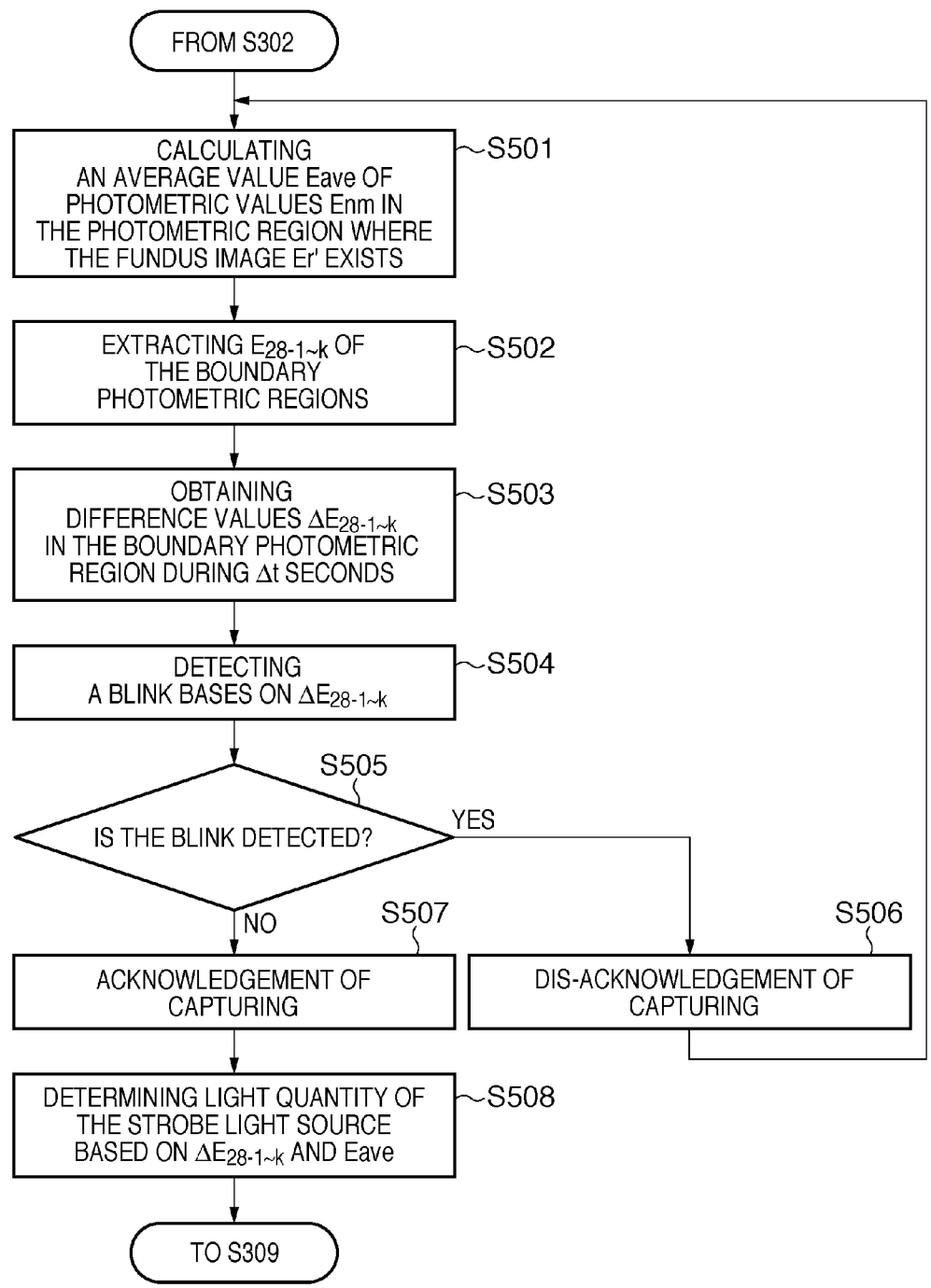
FIG. 5 shows a flow chart indicating the capture permit determination process in the second embodiment.

FIG. 4 shows the status of image formation of the fundus Er of the eye E, which is illuminated by the infrared LED 14 of the observation light source, as the fundus image Er' on the image sensing device 5. Further, FIG. 5 is a flowchart for describing the process of the capturing acknowledgement determination unit 27, which replaces the steps, S303 to S308 in FIG. 3. A boundary photometric region 28 indicated with hatched lines within N×M optometric regions in FIG. 4 is a region where a surrounding part K of the fundus image Er' (a boundary of the edge part) exists. The number of the boundary photometric regions 28 is assumed to be k. In addition, generally speaking, a fundus image Er' is formed at the regular position on the image. That is, the region of the fundus image and the boundary photometric region 28 are placed at the predetermined region because the fundus image is formed at the regular point.

As described in the first embodiment, the capturing acknowledgement determination unit 27 receives N×M photometric values Enm every $\Delta t$ seconds from the photometric value calculation unit 17 (S302 in FIG. 3). Further, every predetermined time T (for example, ⅕ seconds) the capturing acknowledgement determination unit 27 performs the following steps:

calculating the average of the photometric values Eave of the region (the boundary photometric region 28 and the inner photometric region in FIG. 4) where the fundus image Er' exists at t=T (S501).

extracting the boundary photometric values corresponding to k piece of the boundary photometry regions 28, $E_{28-1}$, $E_{28-2}, E_{28-3}, \ldots E_{28-k}$ from among the photometric values Enm (S502).

calculating the temporal variation during $\Delta t$ seconds with respect to each of the boundary region photometric values using the equation: $\Delta E_{28-x} = E_{28-x}(t=T+\Delta t) - E_{28-x}(t=T)$ (S503).

further, the capturing acknowledgement determination unit 27 determines whether or not the amount of light changes by the blink based on $\Delta E_{28-x}$ (x=1, 2, ..., k) (S504). For instance, the capturing acknowledgement determination unit 27 determines that the amount of light variation of the fundus image Er' is caused by the blink if at least one of the fundus images, $\Delta E_{28-x}$ (x=1, 2, ..., k) is larger than the predetermined value, then returns the output of capturing dis-acknowledgement to the control unit 18 (S504, S505, S506). On the other hand, if all of $\Delta E_{28-x}$ (x=1, 2, ..., k) is smaller than the predetermined value, the capturing acknowledgement determination unit 27 determines that the light amount variation of the fundus image Er' is not caused by the blink, and returns the output of capturing acknowledgement to the control unit 18 (S504, S505, S507). Further, the control unit 18 determines the light quantity of the strobe light source by using $E_{28-x}$ (x=1, 2, ..., k) obtained at S502 and Eave calculated at S501 (S508). For instance, the control unit 18 compares k pieces of the boundary region photometric values $E_{28-x}$ (x=1, 2, ..., k) with the photometric average value Eave. Further, the control unit 18 eliminates the boundary region photometric values $E_{28-x}$ which are brighter than the predetermined ratio from the photometric value Enm. Then the control unit 18 determines the light quantity of the strobe light source 12 based on the remained photometric values and the control status of the observation light source control unit 24 and controls the imaging light source control unit 23. That is, the light quantity is determined by eliminating the photometric values which are larger than the predetermined threshold determined by the averaged photometric values in the photometric region including the fundus image Er' among the photometric values in the photometric region corresponding to the edge of the fundus image Er'.

As mentioned above, according to the second embodiment, the photometric value of the k regions (boundary region photometric value $E_{28-x}$), where the surrounding part of the fundus image Er' exists, are acquired. Then, the blink detection is performed by using the k pieces of the boundary region photometric values. Accordingly, in the second embodiment, the load of processing can be reduced compared to the first embodiment. Moreover, by comparing the photometric values $E_{28-x}$ in the boundary region and the photometric average value Eave of fundus image Er', the effect on determining light quantity of the strobe light source, which is caused by the reflected light (flare) from the examined eye, can be eliminated, wherein the reflected light is generated by the misalignment and the like between the examined eye and the fundus camera. That is, the light amount enabling obtainment of the central area of the fundus image having excellent brightness can be set by eliminating the effect of the reflected light from the examined eye when determining the light amount of the strobe light source 12 as an imaging light source, even if there is the reflected light of illumination light around the fundus image from the eye to be examined. Indeed, it is possible to attain the accurate automatic capturing light amount control because the observation light amount control is performed by eliminating the photometric values including the reflected light caused by the misalignment of the position.

Further, at S505, capturing acknowledgement is determined based on the temporal variation of the photometric values, wherein it is determined that a blink is not detected if all the $\Delta E_{28-x}$ (x=1~k) are smaller than the predetermined value. At S505, in addition to or instead of the above determination, the capturing acknowledgement may be determined by a distribution of the photometric values on the image. For instance, the capturing acknowledgement or dis-acknowledgement may be determined by detecting whether or not the misalignment described above exists (presence of the influence of flare). That is, in the boundary region photometric values $E_{28-x}$ (x=1~k), the boundary region photometric values, which are brighter than the predetermined percentage of the photometry average value Eave, is determined as reflected light (flare), caused by misalignment between the eye E and the fundus camera. Further, the capturing acknowledgement determination unit 27 may return the output of capturing dis-acknowledgement to the control unit 18 when there is the reflected light caused by the misalignment. In this way, the capturing acknowledgement/dis-acknowledgement can also be determined by detecting the state of the alignment from the boundary region photometric value $E_{28-x}$. Further, at S504, the capturing acknowledgement/dis-acknowledgement may be determined by detecting the blink in accordance with the procedure (S303, S304) in the first embodiment (blink detection using all photometric values Enm), and combining the blink detection by determining misalignment as described above.

Third Embodiment

Figure 6:
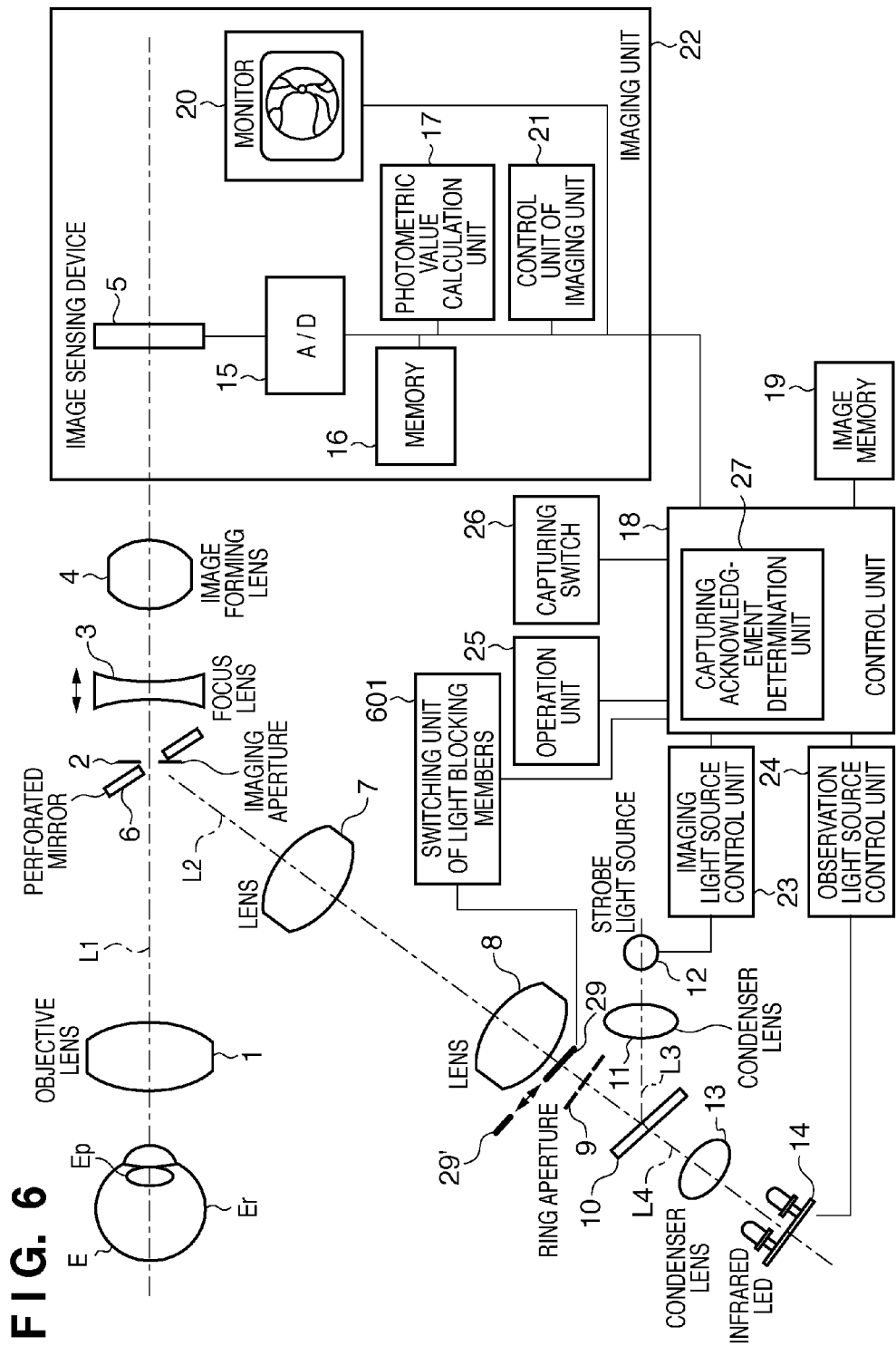
FIG. 6 shows an exemplary configuration for ophthalmic imaging apparatus in the third embodiment.
Figure 7:
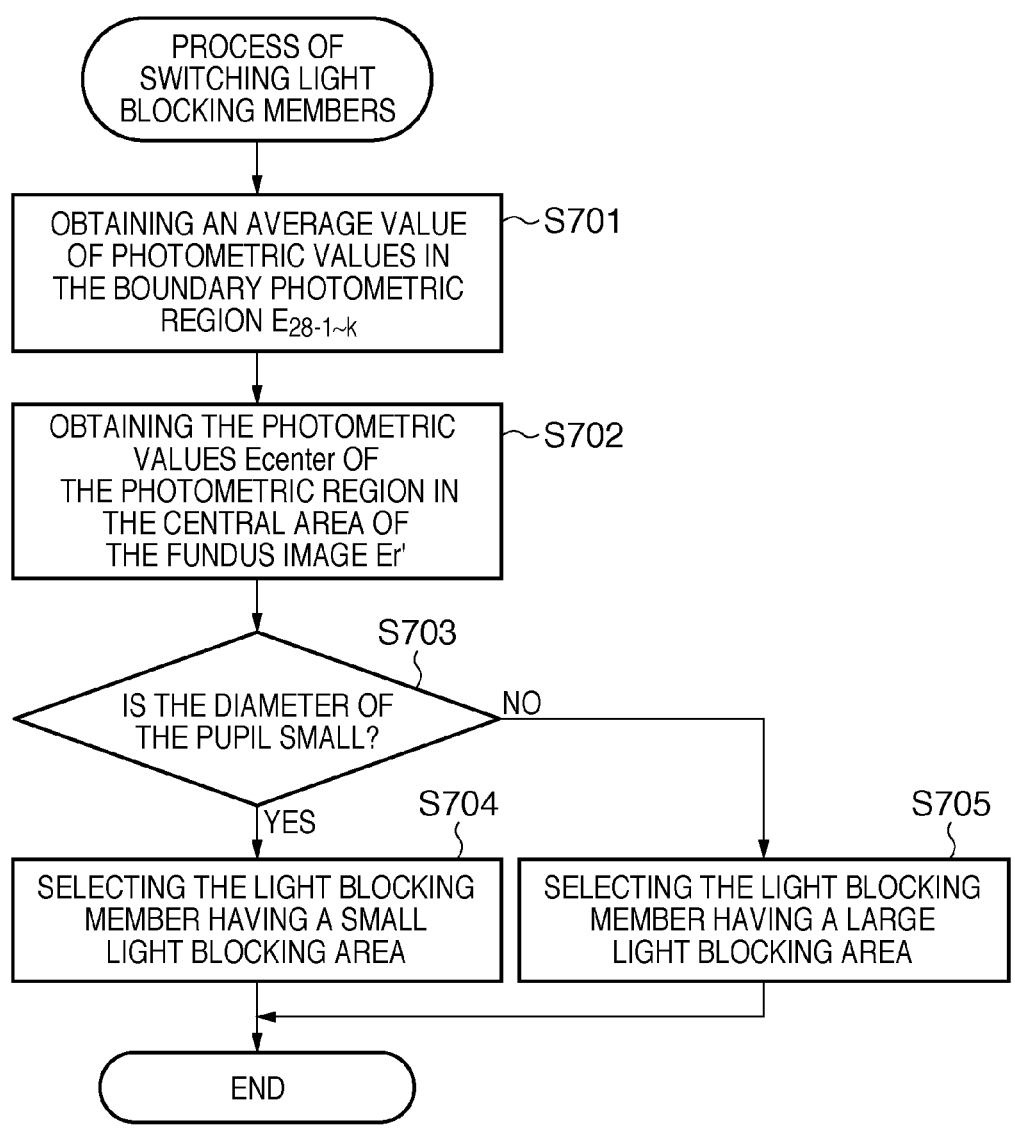
FIG. 7 shows a flow chart indicating the process for switching light blocking members in the third embodiment.

Next, the fundus camera in the third embodiment is described. The third embodiment describes a fundus camera that can obtain a central area of a fundus image with excellent brightness even if the pupil diameter of the eye to be examined is small. FIG. 6 shows a configuration for the fundus camera in the third embodiment. Elements of the structure in FIG. 6 having the same symbols in FIG. 1 mean the same as the first embodiment. Further, FIG. 7 shows a flow chart indicating the process for switching light blocking members in the third embodiment.

Light blocking members arranged on the optical path L2 are structure elements which show structure different from the first embodiment (FIG. 1). The light blocking member is arranged on the upper side of the ring aperture 9, which is allocated at an optically conjugated position for the pupil Ep of the eye E and has an aperture in a ring-shape with a light blocking part at the center of the optical axis. The first light blocking member 29 has a light blocking part at the center which is arranged at an optically conjugated position for the rear surface of lens of the examined eye. Further, a second light blocking member 29' switchable with the first light blocking member 29 is allocated, wherein the second light blocking member 29' has the blocking part smaller than that of the first light blocking member 29. A switch unit 601 of light blocking members, under control of the control unit 18, switches light blocking members so as to selectively arrange the first light blocking member 29 or the second light blocking member 29' on the optical axis L2.

It is assumed that a fundus image Er' of the fundus Er of the eye E, which is illuminated by the infrared LED 14 of the observation light source, is formed on the image sensing device 5, and it is also assumed that a pupil diameter of eye E is small. In this case, a central area of the formed fundus image Er' on the image sensing device 5 is darker than the surrounding area of the fundus image because of the ring-shaped illumination light beam. That is, an unevenness of illumination is generated by the pupil.

Therefore, the control unit 18 performs the following steps:
calculating an average value of photometric values (boundary region photometric values $E_{28-1-k}$) in the surrounding area of fundus image Er' of the photometric values Enm (S701).
obtaining a photometric value of the central area Ecenter of the fundus image Er' from the photometric values Enm (S702).
After comparing the average value calculated at S701 with the photometric value Ecenter obtained at S702, determining that the pupil has a small diameter if the brightness indicated by photometric values of the central area is darker than the predetermined ratio (S703). For instance, the pupil is determined to have a small diameter if Ecenter is smaller than ((average value calculated at S701)×α), wherein α<1.

In addition, although the average value of the photometric values is used for determining as described above, a maximum value or minimum value can be used for it. Although the boundary metric value and the photometric value of the central area are compared, as described above, the comparison is not limited to this method. For instance, it is possible to determine that the pupil has a small diameter when the brightness indicated by the photometric value of the center is darker than the prescribed ratio as the result of comparing the photometric value of the central area Ecenter and the photometric average value Eave of the region where the fundus image exists. Alternatively, it is possible to determine that the pupil has a small diameter when the brightness indicated by the photometric value of the center is darker than the prescribed ratio as the result of comparing the photometric value of the central area with the photometric values of the middle angle region existing between the central area and the surrounding area of the fundus image (region where the central area is excluded from the region of the fundus image). Moreover, it may use a method combining some or all of the various types of comparison methods as described above. In addition, the photometric value of the photometric region corresponding to the gravity point (central point) of the fundus image Er', or the averaged photometric value of the predetermined number of the photometric region near the gravity point (central point) and the like, can be used as the photometric value of the central area Ecenter of the fundus image Er'.

The control unit 18 controls the switch unit 601 of light blocking members to arrange the second light blocking member 29' having a blocking area smaller than the first light blocking member 29 on the optical axis L2 if it is determined that the central area is dark (S703, S704). On the other hand, the control unit 18 controls the switch unit 601 of light blocking members to arrange the first light blocking member 29 on the optical axis L2 (S705) if it is determined that the central area is not dark (the pupil is not small). After this operation, the control unit 18 waits for the output of the capturing acknowledgement from the capturing acknowledgement determination unit 27. Descriptions regarding the capturing acknowledgement determined by the capturing acknowledgement determination unit 27, the light amount setting of the strobe light source 12 and others are the same as the first and second embodiments.

As mentioned above, according to the third embodiment, the capturing acknowledgement determination unit 27 determines that capturing is not permitted because of the illumination unevenness caused by the small pupil when the brightness indicated by the photometric value of the central area of the fundus image is darker than the surrounding area of the fundus image, the region of the fundus image or the photometric value in the middle angle field. At this operation, the control unit 18 automatically switches the light blocking member arranged in the illumination optical system to the second light blocking member 29' for a small pupil and prompts the capturing acknowledgement determination unit 27 for the capturing acknowledgement. For this reason, it enables to obtain a fundus image having excellent brightness near the central area of the fundus even if the diameter of the pupil of the examined eye is small.

As described above, according to each embodiment, the imaging unit of obtaining a moving image for observing the fundus of the examined eye and the imaging unit of obtaining a still image for the fundus of the examined eye are shared. Further, the imaging unit is also used for a photometric sensor to determine the imaging light amount and a detection sensor for detecting blinks. As seen above, it is possible not to get the apparatus complex by sharing each function of the imaging unit and to realize no relative displacement of an image sensor and each detector. For this reason, the present invention can provide a fundus camera, which enables to automatically control capturing light amount, to detect blinks and to detect illumination unevenness caused by misalignment, blinks and others with low cost but high in accuracy, and to obtain a fundus image having excellent brightness without capturing failure.

According to each embodiment, the ophthalmic imaging apparatus, which enables to perform blink detection with the simple structure, can be provided.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided for the computer for example via a network or from a recording medium of various types serving as the memory device (e.g., computer-readable storage medium).

While the present invention has been described with reference to exemplary embodiments, it is to be understood that the invention is not limited to the disclosed exemplary embodiments. The scope of the following claims is to be accorded with the broadest interpretation so as to encompass all such modifications and equivalent structures and functions.

This application claims the benefit of Japanese Patent Application No. 2010-126293, filed Jun. 1, 2010, which is hereby incorporated by reference herein in its entirety.

What is claimed is:

1. An ophthalmic apparatus comprising:
an imaging unit configured to execute moving image capturing and still image capturing to obtain a moving image and a still image of a fundus image; and
a control unit configured to control the still image capturing based on a comparison of a first photometric value in a first frame image of the moving image obtained by the moving image capturing with a second photometric value in a second frame image of the moving image obtained by the moving image capturing.

2. The apparatus according to claim 1, wherein said control unit inhibits the still image capturing in a case where a difference value between the first photometric value and the second photometric value is greater than a predetermined value.

3. The apparatus according to claim 2, wherein said control unit permits the still image capturing in a case where a difference value between the first photometric value and the second photometric value is smaller than a predetermined value.

4. The apparatus according to claim 2, wherein said control unit (a) obtains a third photometric value in a third frame image of the moving image and a fourth photometric value in a fourth frame image of the moving image after it is determined that the difference value between the first photometric value and the second photometric value is greater than a predetermined threshold value, (b) compares the third photometric value and the fourth photometric value, and (c) permits the still image capturing in a case where a difference value between the third photometric value and the fourth photometric value is greater than a predetermined value.

5. The apparatus according to claim 2, wherein said control unit (a) obtains a third photometric value in a third frame image of the moving image and a fourth photometric value in a fourth frame image of the moving image after it is determined that the difference value between the first photometric value and the second photometric value is greater than a predetermined threshold value, (b) compares the third photometric value and the fourth photometric value, and (c) automatically executes the still image capturing in a case where a difference value between the third photometric value and the fourth photometric value is greater than a predetermined value.

6. The apparatus according to claim 1, wherein said control unit permits the still image capturing in a case where a difference value between the first photometric value and the second photometric value is smaller than a predetermined value.

7. The apparatus according to claim 1, wherein the first frame image and the second frame image are consecutive images in time.

8. The apparatus according to claim 1, wherein said control unit determines that a blink occurred in a case where the difference value between the first photometric value and the second photometric value is larger than a predetermined value.

9. The apparatus according to claim 8, wherein said control unit (a) obtains a third photometric value in a third frame image of the moving image and a fourth photometric value in a fourth frame image of the moving image after it is determined that a blink occurred, (b) compares the third photometric value and the fourth photometric value, and (c) permits the still image capturing in a case where a difference value between the third photometric value and the fourth photometric value is greater than a predetermined value.

10. The apparatus according to claim 8, wherein said control unit (a) obtains a third photometric value in a third frame image of the moving image and a fourth photometric value in a fourth frame image of the moving image after it is determined that a blink occurred, (b) compares the third photometric value and the fourth photometric value, and (c) automatically executes the still image capturing in a case where a difference value between the third photometric value and the fourth photometric value is greater than a predetermined value.

11. A method of controlling an ophthalmic apparatus comprising the steps of:
    executing moving image capturing and still image capturing to obtain a moving image and a still image of a fundus image; and
    controlling the still image capturing based on a comparison of a first photometric value in a first frame image of the moving image obtained by the moving image capturing with a second photometric value in a second frame image of the moving image obtained by the moving image capturing.

12. The method according to claim 11, wherein, in the step of controlling, the still image capturing is inhibited in a case where a difference value between the first photometric value and the second photometric value is greater than a predetermined value.

13. The method according to claim 12, wherein, in the step of controlling, the still image capturing is permitted in a case where a difference value between the first photometric value and the second photometric value is smaller than a predetermined value.

14. The method according to claim 12, wherein the step of controlling includes the steps of:
    obtaining a third photometric value in a third frame image of the moving image and a fourth photometric value in a fourth frame image of the moving image after it is determined that the difference value between the first photometric value and the second photometric value is greater than a predetermined threshold value;
    comparing the third photometric value and the fourth photometric value; and
    permitting the still image capturing in a case where a difference value between the third photometric value and the fourth photometric value is greater than a predetermined value.

15. The method according to claim 12, wherein the step of controlling includes:
    obtaining a third photometric value in a third frame image of the moving image and a fourth photometric value in a fourth frame image of the moving image after it is determined that the difference value between the first photometric value and the second photometric value is greater than a predetermined threshold value;
    comparing the third photometric value and the fourth photometric value; and
    automatically executing the still image capturing in a case where a difference value between the third photometric value and the fourth photometric value is greater than a predetermined value.

16. The method according to claim 11, wherein, in the step of controlling, the still image capturing is permitted in a case where a difference value between the first photometric value and the second photometric value is smaller than a predetermined value.

17. The method according to claim 11, wherein the first frame image and the second frame image are consecutive images in time.

18. The method according to claim 11, wherein, in the step of controlling, it is determined that a blink occurred in a case where the difference value between the first photometric value and the second photometric value is larger than a predetermined value.

19. The method according to claim 18, wherein the step of controlling includes the steps of:
    obtaining a third photometric value in a third frame image of the moving image and a fourth photometric value in a fourth frame image of the moving image after it is determined that a blink occurred;
    comparing the third photometric value and the fourth photometric value; and
    permitting the still image capturing in a case where a difference value between the third photometric value and the fourth photometric value is greater than a predetermined value.

20. The method according to claim 18, wherein the step of controlling includes the steps of:
    obtaining a third photometric value in a third frame image of the moving image and a fourth photometric value in a fourth frame image of the moving image after it is determined that a blink occurred;
    comparing the third photometric value and the fourth photometric value; and
    automatically executing the still image capturing in a case where a difference value between the third photometric value and the fourth photometric value is greater than a predetermined value.

21. A non-transitory storage medium storing a program for causing a computer to execute the method according to claim 11.

* * * * *